(12) United States Patent
Futami et al.

(10) Patent No.: US 8,280,129 B2
(45) Date of Patent: Oct. 2, 2012

(54) MEDICAL IMAGE MANAGEMENT DEVICE AND MEDICAL IMAGE SYSTEM CORRELATING IMAGES FROM PAST AND PRESENT EXAMINATIONS

(75) Inventors: Hikaru Futami, Otawara (JP); Kenichi Niwa, Otawara (JP); Muneyasu Kazuno, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 835 days.

(21) Appl. No.: 12/260,395

(22) Filed: Oct. 29, 2008

(65) Prior Publication Data
US 2009/0116710 A1    May 7, 2009

(30) Foreign Application Priority Data
Nov. 2, 2007    (JP) .................. 2007-286575

(51) Int. Cl.
*C12N 15/63* (2006.01)
(52) U.S. Cl. .................. 382/128; 702/21
(58) Field of Classification Search .......... 382/123–128; 700/474; 707/3
See application file for complete search history.

(56) References Cited

U.S. PATENT DOCUMENTS

| | | | | |
|---|---|---|---|---|
| 5,825,941 A * | 10/1998 | Linford et al. | ............ | 382/294 |
| 7,383,511 B2 * | 6/2008 | Tanaka et al. | ............ | 715/748 |
| 7,676,072 B2 * | 3/2010 | Sugiyama | ............ | 382/128 |
| 2002/0172405 A1 * | 11/2002 | Schultz | ............ | 382/128 |
| 2004/0082845 A1 * | 4/2004 | Matsumoto et al. | ............ | 600/407 |
| 2007/0081700 A1 * | 4/2007 | Blumenfeld et al. | ............ | 382/128 |
| 2007/0081707 A1 * | 4/2007 | Sirohey et al. | ............ | 382/128 |
| 2007/0133850 A1 * | 6/2007 | Paez | ............ | 382/128 |
| 2007/0223797 A1 * | 9/2007 | Kaneko | ............ | 382/128 |
| 2007/0238963 A1 | 10/2007 | Kaminaga et al. | | |
| 2007/0239489 A1 | 10/2007 | Masuzawa et al. | | |
| 2008/0118118 A1 * | 5/2008 | Berger | ............ | 382/128 |
| 2008/0181472 A1 * | 7/2008 | Doi et al. | ............ | 382/128 |
| 2008/0201372 A1 | 8/2008 | Fukatsu et al. | | |
| 2008/0212854 A1 | 9/2008 | Fukatsu et al. | | |
| 2008/0219537 A1 | 9/2008 | Matsue et al. | | |
| 2008/0226144 A1 * | 9/2008 | Squilla et al. | ............ | 382/128 |
| 2008/0253629 A1 * | 10/2008 | Kazuno et al. | ............ | 382/128 |

FOREIGN PATENT DOCUMENTS

JP    2007-167634    7/2007
WO    WO 2007/061099 A1    5/2007

OTHER PUBLICATIONS

U.S. Appl. No. 12/107,356, filed Apr. 22, 2008, Muneyasu Kazuno, et al.

* cited by examiner

*Primary Examiner* — Nathan Ha
(74) *Attorney, Agent, or Firm* — Oblon, Spivak, McClelland, Maier & Neustadt, L.L.P.

(57) ABSTRACT

A medical image managing device can be used in a medical image system in which an image storage device storing medical images obtained by an imaging device as past images so as to specify an examination and a series and one or more image reference devices referring a user to the past images stored in the image storage device are connected to each other through a network.

25 Claims, 18 Drawing Sheets

FIG. 7

| EXAMINA-TION ROOM | MODALITY | | VIEWER | |
|---|---|---|---|---|
| | DEVICE TYPE | AE TITLE | NAME OF DEVICE | MAC ADDRESS |
| 1 | CT | TO_CT_CLIN_A | VIEWER 1 | 12_34_AB_CD |
| | | | VIEWER 2 | 56_78_EF_GH |
| 2 | CT | TO_CT_CLIN_B | VIEWER 3 | 13_58_A1_B2 |
| 3 | MRI | TO_MRI_CLIN_A | VIEWER 4 | 34_56_C1_D2 |
| : | : | : | : | : |

FIG. 8

| MODALITY | PRIORITY ORDER | ITEM |
|---|---|---|
| CT | 1 | CONTRAST |
| | 2 | CONTRASTING SITE |
| | 3 | PHOTOGRAPHING DIRECTION |
| | 4 | RECONSTRUCTION FUNCTION |
| | 5 | SLICE THICKNESS |
| | 6 | HELICAL PITCH |
| | 7 | TUBE CURRENT |
| | 8 | TUBE VOLTAGE |
| MRI | 1 | CONTRAST |
| | 2 | PHOTOGRAPHING SITE |
| | 3 | RECONSTRUCTION FUNCTION |
| | 4 | SLICE THICKNESS |
| | : | : |

FIG. 9

| EXAMINATION ROOM | EXAMINATION FRAME | | | | | |
|---|---|---|---|---|---|---|
| | 1 | 2 | 3 | 7 | 8 | ... |
| 1 | 09:30~09:50 | 10:00~10:20 | 10:30~10:50 | 13:30~13:50 | 14:10~14:30 | : |
| 2 | 09:00~09:20 | 09:30~09:50 | 10:00~10:20 | 13:00~13:20 | 13:30~13:50 | : |
| : | : | : | : | : | : | |

FIG. 11

| MODALITY | | PHOTOGRAPHING ORDER | TRANSMISSION ORDER |
|---|---|---|---|
| DEVICE TYPE | AE TITLE | | |
| CT | TO_CT_CLIN_A | 1→2→···→10 | 10→9→···1 |
| CT | TO_CT_CLIN_B | 1→2→···→10 | 1→2→···→10 |
| MRI | TO_MRI_CLIN_A | 1→2→···→10 | 10→8→···→2→9→7→···→1 |

FIG. 12

| MODALITY | PHOTOGRAPH-ING SITE | IMAGE GENERATING CONDITION (RECONSTRUCTION CONDITION) | PHOTOGRAPH-ING DIRECTION | PHOTOGRAPHING CONDITION | | SLICE THICKNESS [mm] | RECONSTRUCTION FUNCTION |
|---|---|---|---|---|---|---|---|
| | | | | TUBE CURRENT [mA] | TUBE VOLTAGE [kV] | | |
| CT | CHEST | Axial 1 | Axial | 300 | 120 | 0.5 | FC1 |
| | | Axial 2 | Axial | 150 | 100 | 1 | FC2 |
| | | : | : | : | : | : | : |
| | | Sagittal 1 | Sagittal | 300 | 120 | 1 | FC1 |
| | | Sagittal 2 | Sagittal | 150 | 100 | 1.5 | FC2 |
| | | : | : | : | : | : | : |
| | ABDOMEN | Axial 8 | Axial | 300 | 120 | 2 | FC8 |
| | : | : | : | : | : | : | : |
| MR | HEAD | Oblique T1 | Oblique | – | – | 3 | T1 |
| | | Oblique T2 | Oblique | – | – | 3 | T2 |
| | | : | : | : | : | : | : |
| | : | : | : | : | : | : | : |
| : | : | : | : | : | : | : | : |

FIG. 13

| MODALITY | PHOTOGRAPH-ING SITE | PHOTOGRAPH-ING PLAN | IMAGE GENERATING CONDITION (RECONSTRUCTION CONDITION) |
|---|---|---|---|
| CT | CHEST | PLAN 1 | Axial 1 |
| | | | Axial 2 |
| | | | Axial 3 |
| | | | Axial 4 |
| | | PLAN 2 | Axial 1 |
| | | | Axial 2 |
| | | | Axial 3 |
| | | | Sagittal 1 |
| | | | Sagittal 2 |
| | | PLAN 3 | Axial 3 |
| | | ⋮ | ⋮ |
| | ABDOMEN | PLAN 1 | Axial 8 |
| | | | Axial 9 |
| | | | Axial 10 |
| | | ⋮ | ⋮ |
| | ⋮ | ⋮ | ⋮ |
| MR | HEAD | PLAN 1 | Oblique T1 |
| | | | Oblique T2 |
| | | ⋮ | ⋮ |
| ⋮ | ⋮ | ⋮ | ⋮ |

FIG. 14

| MODALITY | PHOTOGRAPHING SITE | IMAGE GENERATING CONDITION (RECONSTRUCTION CONDITION) | DEVICE VERSION VENDOR | | | |
|---|---|---|---|---|---|---|
| | | | A64 | A64_V3.0 | A16 | ... |
| CT | CHEST | Axial 1 | Axial 1 | Axial 1 | Axial 4 | ... |
| | | Axial 2 | Axial 2 | Axial 3 | Axial 5 | ... |
| | | : | : | : | : | : |
| | | Sagittal 1 | Sagittal 1 | Sagittal 1 | Sagittal 4 | : |
| | | Sagittal 2 | Sagittal 2 | Sagittal 3 | Sagittal 5 | : |
| | | : | : | : | : | : |
| | ABDOMEN | Axial 8 | Axial 8 | Axial 9 | Axial 10 | : |
| | : | : | : | : | : | : |
| | | | Van | VanAt | VanSP | ××× |
| MR | HEAD | Oblique T1 | Oblique T1 | Oblique T1 | Oblique T2 | : |
| | | Oblique T2 | Oblique T2 | Oblique T3 | Oblique T1 | : |
| | : | : | : | : | : | : |

FIG. 15

| MODALITY | PHOTOGRAPH-ING SITE | PHOTOGRAPH-ING PLAN | DEVICE VERSION VENDOR | | | |
|---|---|---|---|---|---|---|
| | | | A64 | A64_V3.0 | A16 | ... |
| CT | CHEST | PLAN 1 | PLAN 1 | PLAN 2 | PLAN 1 | .. |
| | | PLAN 2 | PLAN 2 | PLAN 1 | PLAN 3 | .. |
| | | .. | .. | .. | .. | .. |
| | ABDOMEN | PLAN 1 | PLAN 1 | PLAN 3 | PLAN 4 | .. |
| | .. | .. | .. | .. | .. | .. |
| | | | DEVICE VERSION VENDOR | | | |
| | | | Van | VanAt | VanSP | ... |
| MR | HEAD | PLAN 1 | PLAN 1 | PLAN 2 | PLAN 1 | .. |
| | .. | .. | .. | .. | .. | .. |

FIG. 16

| VIEWER | | PATIENT ID | REFERENCE IMAGE INFORMATION | | REFERENCE DATE | | REFERENCE ORDER |
|---|---|---|---|---|---|---|---|
| NAME OF DEVICE | MAC ADDRESS | | EXAMINATION UID | SERIES UID | DATE | TIME | |
| VIEWER 1 | 12_34_AB_CD | 12345678 | 12.345.xxxxxxxxxxxx.2 | 12.345.xxxxxxxxxxxxx.2.1 | 2007/08/02 | 10:30 | 1 |
| | | | | 12.345.xxxxxxxxxxxxx.2.2 | 2007/08/02 | 10:35 | 2 |
| | | | | 12.345.xxxxxxxxxxxxx.2.3 | 2007/08/02 | 10:40 | 3 |
| VIEWER 2 | 56_78_EF_GH | 12345678 | 12.345.xxxxxxxxxxxx.0 | 12.345.xxxxxxxxxxxxx.0.1 | 2007/07/30 | 09:20 | 1 |
| | | | | 12.345.xxxxxxxxxxxxx.0.2 | 2007/07/30 | 09:25 | 2 |
| | | | | 12.345.xxxxxxxxxxxxx.0.3 | 2007/07/30 | 09:40 | 3 |
| VIEWER 3 | 13_58_A1_B2 | 45678910 | 12.456.xxxx.xxxxx.x.xx.1 | 12.456.xxxxxxxxxxxxx.5.3 | 2007/08/02 | 10:25 | 1 |
| | | | | 12.456.xxxxxxxxxxxxx.5.2 | 2007/08/02 | 10:30 | 2 |
| | | | | 12.456.xxxxxxxxxxxxx.5.4 | 2007/08/02 | 10:35 | 3 |
| | | | | 12.456.xxxxxxxxxxxxx.5.1 | 2007/08/02 | 10:40 | 4 |
| : | : | : | : | : | : | : | : |

FIG. 18

PRESENT EXAMINATION A

| DEVICE TYPE | CT | | | |
|---|---|---|---|---|
| AE TITLE | TO_CT_CLIN_A | | | |
| PATIENT ID | 12345678 | | | |
| SERIES No. | IMAGE GENERATING CONDITION (RECONSTRUCTION CONDITION) | PHOTO-GRAPHING SITE | CONTRAST AGENT | PHOTOGRAPHING DATE |
| | | | | DATE | TIME |
| SERIES 1 | Axial 1 | CHEST | NONE | 2007/08/02 | 10:35 |
| SERIES 2 | Axial 2 | CHEST | NONE | 2007/08/02 | 10:40 |
| SERIES 3 | Axial 3 | CHEST | NONE | 2007/08/02 | 10:45 |

PRESENT EXAMINATION B

| DEVICE TYPE | CT | | | |
|---|---|---|---|---|
| AE TITLE | TO_CT_CLIN_A | | | |
| PATIENT ID | 12345678 | | | |
| SERIES No. | IMAGE GENERATING CONDITION (RECONSTRUCTION CONDITION) | PHOTO-GRAPHING SITE | CONTRAST AGENT | PHOTOGRAPHING DATE |
| | | | | DATE | TIME |
| SERIES 1 | Axial 2 | CHEST | NONE | 2007/08/02 | 14:20 |
| SERIES 2 | Sagittal 2 | CHEST | NONE | 2007/08/02 | 14:25 |
| SERIES 3 | Axial 4 | CHEST | NONE | 2007/08/02 | 14:30 |

PAST EXAMINATION (REFERENCE INFORMATION) C

| DEVICE NAME | VIEWER 1 | | | |
|---|---|---|---|---|
| MAC ADDRESS | 12_34_AB_CD | | | |
| PATIENT ID | 12345678 | | | |
| SERIES No. | REFERENCE DATE | | REFERENCE ORDER | INPUT (SELECTED) IMAGE GENERATING CONDITION |
| | DATE | TIME | | |
| SERIES 1 | 2007/08/02 | 10:30 | 1 | Axial 1 |
| SERIES 2 | 2007/08/02 | 10:35 | 2 | Axial 2 |
| SERIES 3 | 2007/08/02 | 10:40 | 3 | Axial 3 |

PAST EXAMINATION (REFERENCE INFORMATION) D

| DEVICE NAME | VIEWER 2 | | | |
|---|---|---|---|---|
| MAC ADDRESS | 56_78_EF_GH | | | |
| PATIENT ID | 12345678 | | | |
| SERIES No. | REFERENCE DATE | | REFERENCE ORDER | INPUT (SELECTED) PHOTOGRAPHING CONDITION |
| | DATE | TIME | | |
| SERIES 1 | 2007/08/02 | 14:20 | 2 | - |
| SERIES 2 | 2007/08/02 | 14:25 | 3 | - |
| SERIES 3 | 2007/08/02 | 14:15 | 1 | - |

IMAGE INCIDENTAL INFORMATION OF PAST EXAMINATION D

| SERIES No. | CONTRAST AGENT | PHOTOGRAPHING SITE | PHOTOGRAPHING DIRECTION | RECONSTRUCTION FUNCTION |
|---|---|---|---|---|
| SERIES 1 | - | CHEST | Axial | FO4 |
| SERIES 2 | - | CHEST | Axial | FC2 |
| SERIES 3 | - | CHEST | Sagittal | FC2 |

FIG. 22

| PATIENT ID | PRESENT EXAMINATION | | PAST EXAMINATION | |
|---|---|---|---|---|
| | EXAMINATION UID | SERIES UID | EXAMINATION UID | SERIES UID |
| 12345678 | 12.345.xxxx.xxxxx.x.xx.3 | 12.345.xxxxxxxxxx.xxx.3.1 | | |
| | | 12.345.xxxxxxxxxx.xxx.3.2 | | |
| | | 12.345.xxxxxxxxxx.xxx.3.3 | | |
| | | 12.345.xxxxxxxxxx.xxx.3.4 | | |
| | 12.345.xxxx.xxxxx.x.xx.2 | 12.345.xxxxxxxxxx.xxx.2.1 | 12.345.xxxxxxxxxx.x.xx.2 | 12.345.xxxxxxxxxx.xxx.2.1 |
| | | 12.345.xxxxxxxxxx.xxx.2.2 | | 12.345.xxxxxxxxxx.xxx.2.2 |
| | | 12.345.xxxxxxxxxx.xxx.2.3 | | 12.345.xxxxxxxxxx.xxx.2.3 |
| | | | 12.345.xxxxxxxxxx.x.xx.0 | 12.345.xxxxxxxxxx.xxx.0.1 |
| | | | | 12.345.xxxxxxxxxx.xxx.0.2 |
| | | | | 12.345.xxxxxxxxxx.xxx.0.3 |
| 45678910 | 12.456.xxxx.xxxxx.x.xx.5 | 12.456.xxxxxxxxxx.xxx.5.1 | 12.456.xxxxxxxxxx.x.xx.1 | 12.456.xxxxxxxxxx.xxx.5.3 |
| | | 12.456.xxxxxxxxxx.xxx.5.2 | | 12.456.xxxxxxxxxx.xxx.5.2 |
| | | 12.456.xxxxxxxxxx.xxx.5.3 | | 12.456.xxxxxxxxxx.xxx.5.4 |
| | | 12.456.xxxxxxxxxx.xxx.5.4 | | 12.456.xxxxxxxxxx.xxx.5.1 |
| : | : | : | : | : |

MEDICAL IMAGE MANAGEMENT DEVICE AND MEDICAL IMAGE SYSTEM CORRELATING IMAGES FROM PAST AND PRESENT EXAMINATIONS

CROSS-REFERENCE TO RELATED APPLICATIONS

This application is based upon and claims the benefit of priority from prior Japanese Patent Application No. 2007-286575, filed Nov. 2, 2007, the entire contents of which are incorporated herein by reference.

BACKGROUND OF THE INVENTION

1. Field of the Invention

The present invention relates to a medical image system in which an image storage device storing medical images obtained by one or more imaging devices such as an X-ray computer tomography (CT) device and a magnetic resonance imaging (MRI) device and one or more image reference devices referring a user to the medical images stored in the image storage device are connected to each other through a network and a medical image managing device used in the medical image system.

2. Description of the Related Art

A medical image system is known which includes imaging devices (hereinafter referred to as modalities), an image storage device (hereinafter referred to as server), and image reference devices (hereinafter referred to as viewer). In the medical image system, a technique of specifying a previous image referred to at the time of taking an image in the present checkup of the modality in the unit of series and providing an environment facilitating the comparison and interpretation of radiographic images is known (Japanese Unexamined Patent Publication 2007-167634).

In the diagnosis for observing progress, images (hereinafter, referred to as previous image) acquired from the past (previous) examinations or radiographic interpretation reports on the past (previous) examinations might be referred to in the present examination of a patient for determination of imaging plan, imaging coverage, imaging direction, or imaging condition. For example, the imaging coverage, the imaging direction, and the imaging condition might be set to acquire the same images as the past images for the present examination. The acquired images are classified into layers of examination (study), series (indicator for identifying one scanning process or an image constructing process), and image and are managed by a server. A radiographic interpretation report is prepared by a radiologist (physician) on the basis of the acquired images. At this time, an image considered as being important is stored as a key image.

In the related art, there was provided a medical image diagnosis system for generating and managing objects as shared information for reproducing various imaging conditions or radiographic interpretation information on the past examination at the time of examination or preparation of the radiographic interpretation report and effectively utilizing the objects.

In the related art, it is necessary that devices or systems having means for generating and managing objects as the shared information for reproducing various imaging conditions or radiographic interpretation information on the past examination are connected through a network.

Accordingly, in devices or systems that do not have the means for generating and managing objects and are not connected, the past examination or series to be referred to in the present examination is not specified. Therefore, there is difficulty that a radiologist should specify the past image to be compared by subjective judgment, read out the specified past image from the server, correlate the read past image with the image acquired in the present examination in the unit of series, and interpret the image at the time of interpretation of radiographic image.

BRIEF SUMMARY OF THE INVENTION

In view of the above-mentioned situations, it is desired to manage the correlation between a present image and an image referred to in the present imaging on the basis of one or more series images in the past examination.

According to a first aspect of the invention, there is provided a medical image managing device used in a medical image system in which an image storage device storing medical images obtained by an imaging device as past images so as to specify an examination and a series and one or more image reference devices referring a user to the past images stored in the image storage device are connected to each other through a network, the medical image managing device including: examination correlating unit configured to correlate one past examination with the present examination, the correlated past examination being an examination on the past images satisfying two requirements that (1) the past examination is referred to by the image reference device correlated in advance with the imaging device among the one or more image reference devices and that (2) a patient to be imaged is the same; and series correlating unit configured to correlate series included in the present examination and the past examination correlated by the examination correlating unit with each other with reference to imaging conditions of the respective series.

According to a second aspect of the invention, there is provided a medical image system including: one or more photographing devices photographing medical images; an image storage device storing the medical images photographed by the imaging devices as past images so as to specify an examination and a series; one or more image reference devices referring a user to the past images stored in the image storage device; and a medical image managing device. Here, each imaging device includes incidental information generating unit configured to generate incidental information, which includes imaging device identification information for identifying the corresponding imaging device, patient identification information for identifying a patient, and condition information indicating imaging conditions of the series, every examination. Each image reference device includes reference information generating unit configured to generate reference information, which includes reference device identification information for identifying the image reference device and image identification information for identifying the past images referred to by the user, every examination. The medical image managing device includes acquisition unit configured to acquire the incidental information and the reference information, examination correlating unit configured to correlate the examinations corresponding to the incidental information and the reference information with each other, when two requirements that (1) the imaging device and the image reference device specified on the basis of the incidental information and the reference information acquired by the acquisition unit are correlated in advance and that (2) a patient specified on the basis of the incidental information acquired by the acquisition unit is equal to a patient specified on the basis of the reference information acquired by the acquisition unit, and series correlating unit configured to correlate series with reference to the imaging condition specified on the basis of the incidental information acquired by the acquisition unit and the imaging condition specified by the reference information acquired by the acquisition unit.

Additional objects and advantages of the invention will be set forth in the description which follows, and in part will be obvious from the description, or may be learned by practice of the invention. The objects and advantages of the invention may be realized and obtained by unit of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a diagram illustrating an example of a database describing relations between the modality 1 and the viewers 3 and 4 in FIG. 1.

FIG. 8 is a diagram illustrating an example of a database describing information items used to correlating images.

FIG. 9 is a diagram illustrating an example of a database describing an examination frame every examination room.

FIG. 11 is a diagram illustrating an example of a database describing a series transmission order of each modality 1 in FIG. 1.

FIG. 12 is a diagram illustrating an example of a database describing relations of imaging plans or imaging information associated with the modalities 1 in FIG. 1.

FIG. 13 is a diagram illustrating an example of a database describing relations of imaging plans or imaging information associated with the modalities 1 in FIG. 1.

FIG. 14 is a diagram illustrating an example of a database describing correspondence of the imaging plans or the imaging conditions between versions or vendors of the same type of modalities 1.

FIG. 15 is a diagram illustrating an example of a database describing correspondence of the imaging plans or the imaging conditions between versions or vendors of the same type of modalities 1.

FIG. 16 is a diagram illustrating an example of a storage state of reference information in information storage 21*b* in FIG. 6.

FIG. 18 is a diagram illustrating an example of a combination of image incidental information and reference information in the present image and the past image.

FIG. 22 is a diagram illustrating an example of correlation information.

DETAILED DESCRIPTION OF THE INVENTION

Hereinafter, an embodiment of the invention will be described with reference to the accompanying drawings.

Figure 1:
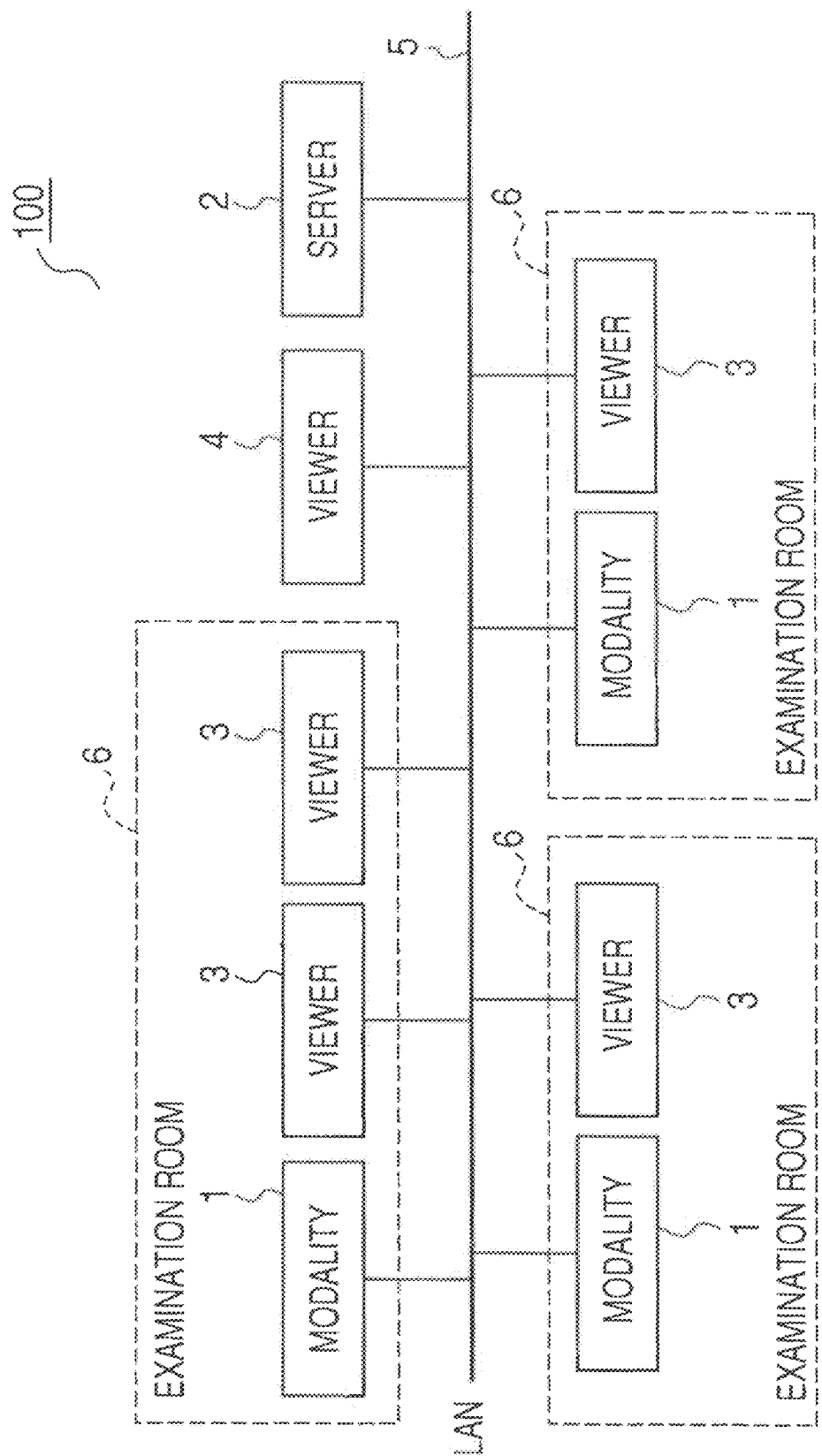
FIG. 1 is a block diagram illustrating a configuration of a medical image system 100 according to an embodiment of the invention.

FIG. 1 is a block diagram illustrating a configuration of a medical image system 100 according to an embodiment of the invention.

The medical image system 100 includes one or more modalities 1, one or more servers 2, one or more viewers 3, and one or more viewers 4, which are connected to each other through a local area network (LAN) 5. The medical image communication between the devices is preferably based on the DICOM (Digital Imaging and Communications in Medicine) standard, but may properly employ another standard. The information communication is, for example, the TCP/IP (Transmission Control Protocol/Internet Protocol) communication of the standard of the field. In this case, data are transmitted in the form of packets through a network.

The modality 1 acquired medical images by imaging a subject. Specifically, the modality 1 reconstructs the medical images (hereinafter, simply referred to as image) of the sample from data acquired scanning the sample. Various types of devices such as an X-ray CT device and an MRI device can be properly used as the modality 1. The modality 1 is installed in one or more examination rooms.

The server 2 stores the images obtained by the modality 1. In this embodiment, the server 2 has a function of a medical image managing device to be described later.

The viewer 3 is installed in one of the examination rooms 6. The viewer 3 acquires and displays the images stored in the server 2 so as to allow a user such as a radiology (radiologic technician) to refer to the past images obtained in the past examinations for the imaging in the present examination.

The viewer 4 is generally installed in a room (for example, radiographic interpretation room) different from the examination rooms 6. The viewer 4 acquires and displays the images stored in the server 2 so as to allow a user such as a radiologist to refer to the images for interpretation.

Figure 2:
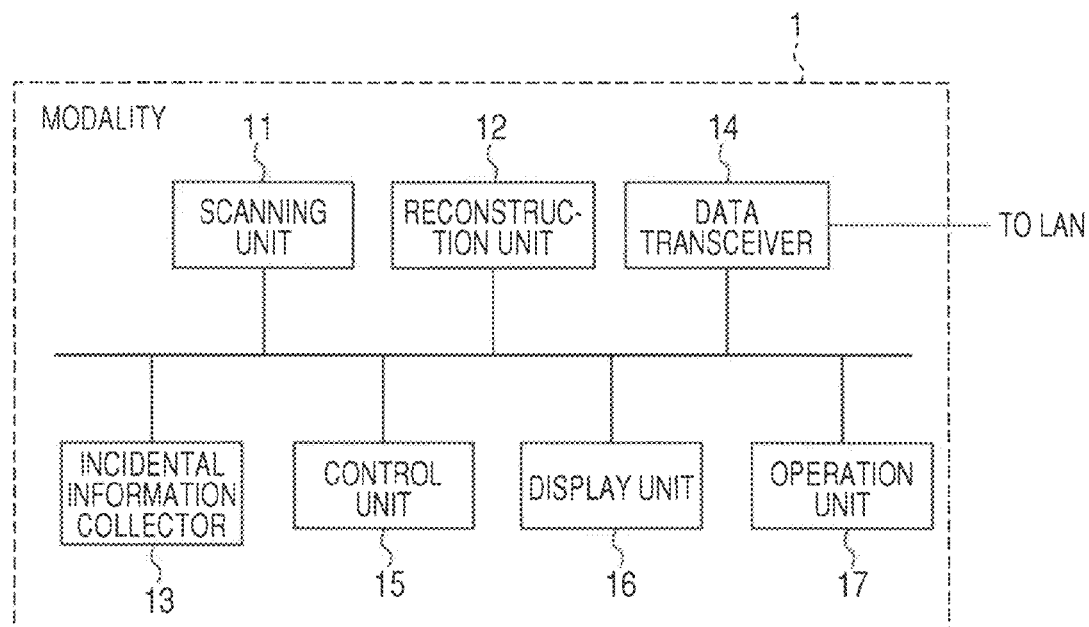
FIG. 2 is a block diagram illustrating a configuration of a modality 1 in FIG. 1.

FIG. 2 is a block diagram illustrating a configuration of the modality 1.

The modality 1 includes a scanning unit 11, a reconstruction unit 12, an incidental information collector 13, a data transceiver unit 14, a control unit 15, a display unit 16, and an operation unit 17.

The scanning unit 11 collects data for reconstructing an image by scanning a sample. The reconstructing unit 12 reconstructs image data on the sample on the basis of the data collected by the scanning unit 11. The incidental information collector 13 collects a variety of information including information indicating the imaging time such as an imaging date or an imaging order in addition to information generally included in the incidental information of the DICOM such as a patient ID, a imaging plan (imaging protocol), imaging information (imaging condition, imaging direction, and reconstruction condition) and generates incidental information including the information pieces. The data transceiver unit 14 includes a LAN board (Ethernet (registered trademark) adaptor). The data transceiver unit 14 transmits a variety of data such as image data or incidental information to the LAN 5. The data transceiver unit 14 receives a variety of data transmitted through the LAN 5. The control unit 15 controls the units of the modality 1 to perform various functions of the modality such as imaging a sample. The display unit 16 displays a variety of information to be provided to a user. The operation unit 17 inputs various instructions or information for operating various functions of the modality 1 in accordance with the user's operation.

Figure 3:
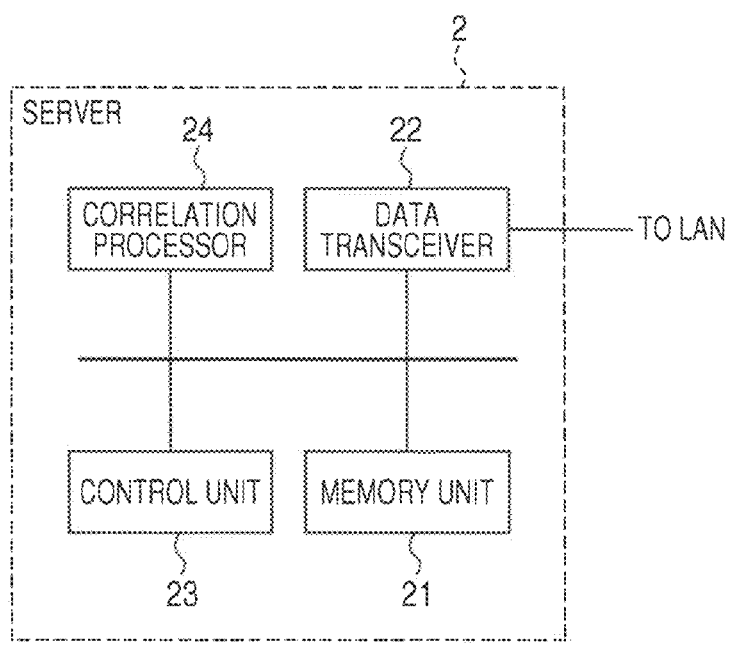
FIG. 3 is a block diagram illustrating a configuration of a server 2 in FIG. 1.

FIG. 3 is a block diagram illustrating a configuration of the server 2.

The server 2 includes a memory unit 21, a data transceiver unit 22, a control unit 23, and a correlation processor 24.

The memory unit 21 stores image data to be stored in the server 2. The data transceiver unit 22 includes a LAN board (Ethernet (registered trademark) adaptor). The data transceiver unit 22 transmits image data to be delivered to the viewers 3 and 4 to the LAN 5 or receives image data transmitted from the modality 1 through the LAN 5. The data transceiver unit 22 receives a variety of information such as reference information and radiographic interpretation information transmitted through the LAN 5. The reference information and the radiographic interpretation information are transmitted from the viewer 3 and the viewer 4. The memory unit 21 is also used to store the reference information, the radiographic interpretation information, and other information. The information stored in the memory unit 21 includes a variety of information to be described necessary for a correlation process of the correlation processor 24. The control unit 23 controls the units of the server 2 to perform various functions of the server such as collecting, managing, and delivering the image data. The correlation processor 24 correlates the images acquired by the new imaging of the modality 1 with the images referred to by the viewers 3 and 4 on the basis of the variety of information stored in the memory unit 21.

Figure 4:
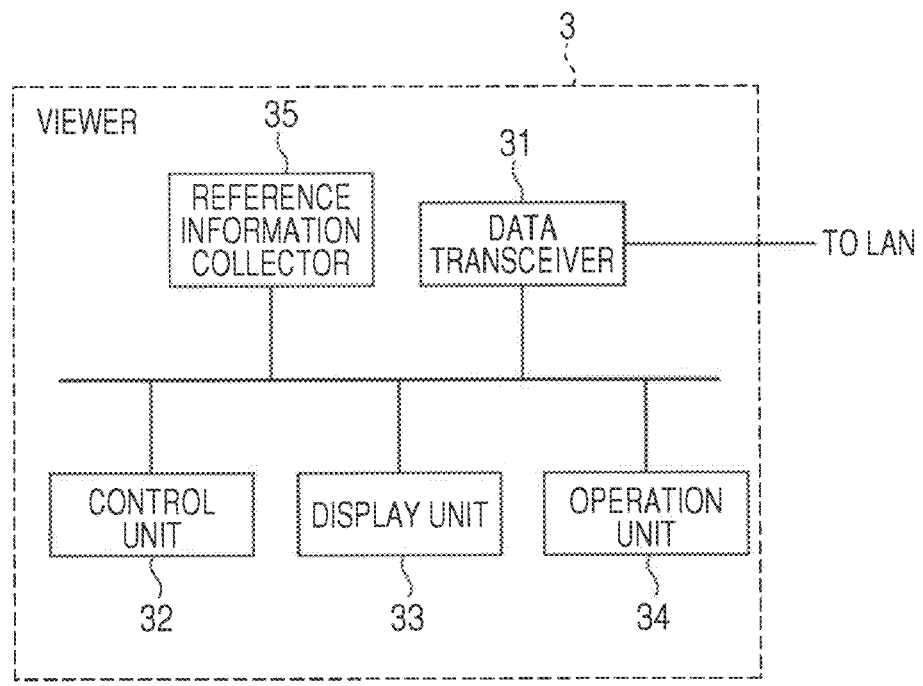
FIG. 4 is a block diagram illustrating a configuration of a viewer 3 in FIG. 1.

FIG. 4 is a block diagram illustrating a configuration of the viewer 3.

The viewer 3 includes a data transceiver unit 31, a control unit 32, a display unit 33, an operation unit 34, and a reference information collector 35.

The data transceiver unit 31 includes a LAN board (Ethernet (registered trademark) adaptor). The data transceiver unit 31 receives image data transmitted from the modality 1 or the server 2 through the LAN 5. The control unit 32 controls the units of the viewer 3 to perform various functions of the viewer such as acquiring image data from the server 2 and displaying images based on the acquired image data. The display unit 33 displays the images based on the image data acquired from the server 2 or a variety of information to be provided to the user. The operation unit 34 inputs various instructions or information for operating various functions of the viewer 3 in accordance with the user's operation. The reference information collector 35 collects a variety of information including at least information indicating the reference time such as a reference date and a reference order and generates reference information including the variety of information. The data transceiver unit 31 transmits various data such as reference information to the LAN 5.

Figure 5:
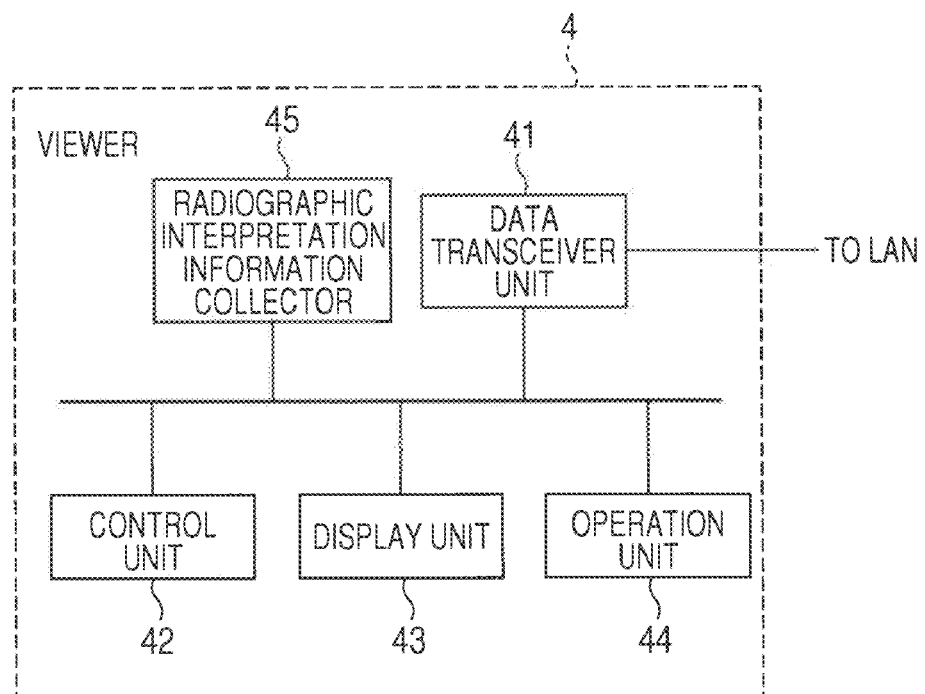
FIG. 5 is a block diagram illustrating a configuration of a viewer 4 in FIG. 1.

FIG. 5 is a block diagram illustrating a configuration of the viewer 4.

The viewer 4 includes a data transceiver unit 41, a control unit 42, a display unit 43, an operation unit 44, and a radiographic interpretation information collector 45.

The data transceiver unit 41 includes a LAN board (Ethernet (registered trademark) adaptor). The data transceiver unit 41 receives image data transmitted from the modality 1 or the server 2 through the LAN 5. The control unit 42 controls the units of the viewer 4 to perform various functions of the viewer such as acquiring image data from the server 2 and displaying images based on the acquired image data. The display unit 43 displays the images based on the image data acquired from the server 2 or a variety of information to be provided to the user. The operation unit 44 inputs various instructions or information for operating various functions of the viewer 4 in accordance with the user's operation. The radiographic interpretation information collector 45 collects a variety of information including at least information indicating the radiographic interpretation time such as a radiographic interpretation date and a radiographic interpretation order and generates radiographic interpretation information including the variety of information. The data transceiver unit 41 transmits various data such as radiographic interpretation information to the LAN 5.

Since the communication in accordance with the TCP/IP standard is made through the LAN 5, the data transceiver units 14, 22, 31, and 41 sequentially pass the information to be transmitted through the layers from an application layer of the TCP/IP, add MAC (Media Access Control) addresses (or adaptor addresses) of the LAN boards disposed in the data transceiver units as a header, encapsulate the information, and then transmit the encapsulated information to the LAN 5 in the unit of packets.

Figure 6:
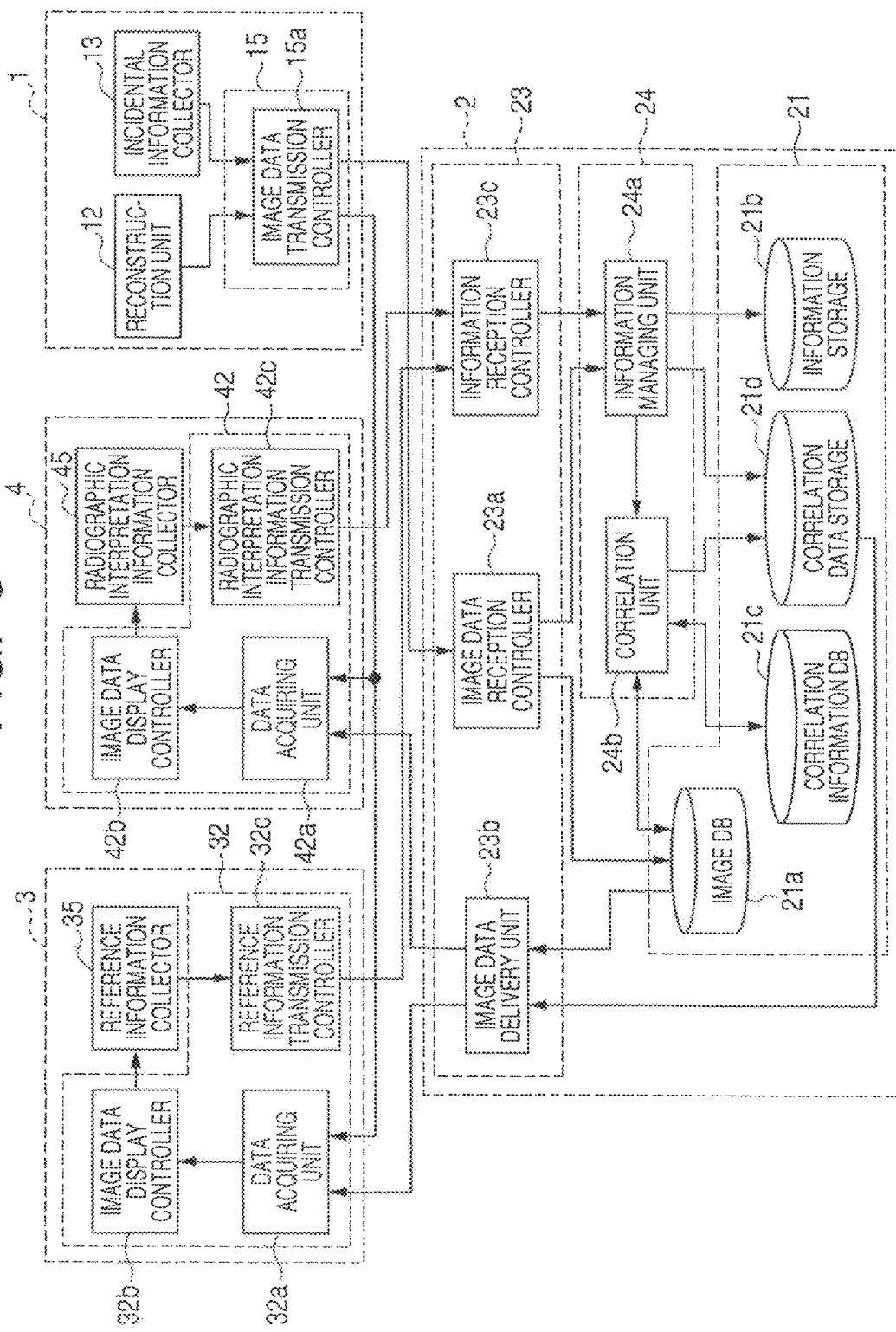
FIG. 6 is a diagram illustrating connection states of devices for correlating the present image with the past images.

FIG. 6 is a diagram illustrating the configurations of the devices for correlating the present image and the past image. The transmission and reception of information between the devices is carried out through the LAN 5 by the data transceiver units 14, 22, 31, and 41, but the flow of information is shown in FIG. 6 with the data transceiver units 14, 22, 31, and 41 and the LAN 5 not shown.

The control units 15, 23, 32, and 42 of the modality 1, the server 2, and the viewers 3 and 4 are all embodied by computers. The control units 15, 23, 32, and 42 serve as various processing units for correlating an image (hereinafter, referred to as present image) newly obtained by the modality 1 with the past images referred to by the viewer 3 in imaging the present image.

The control unit 15 of the modality 1 serves as an image data transmission controller 15*a*. The image data transmission controller 15*a* controls the data transceiver unit 14 to transmit the image data reconstructed by the reconstruction unit 12 to the server 2 or the viewers 3 and 4 along with the incidental information generated by the incidental information collector 13.

The control unit 23 of the server 2 serves as an image data reception controller 23*a*, an image data delivery unit 23*b*, and an information reception controller 23*c*. An image database (image DB) 21*a*, an information storage 21*b*, a correlation information database (correlation information DB) 21*c*, and a correlation data storage 21*d* are established using a part of the memory area of the memory unit 21 of the server 2. The image data reception controller 23*a* controls the data transceiver unit 22 to receive the image data and the incidental information transmitted from the modality 1 and stores the received image data and incidental information in the image database 21*a*. The image data reception controller 23*a* sends the incidental information to the correlation processor 24. The image data delivery unit 23b controls the data transceiver unit 22 to transmit the image data stored in the image database 21a or the correlation data stored in the correlation data storage 21d to the viewers 3 and 4. The information reception controller 23c controls the data transceiver unit 22 to receive the reference information and the radiographic interpretation information transmitted from the viewer 3 and the viewer 4 and sends the received reference information and radiographic interpretation information to the correlation processor 24.

The control unit 32 of the viewer 3 serves as a data acquiring unit 32a, an image data display controller 32b, and a reference information transmission controller 32c. The data acquiring unit 32a controls the data transceiver unit 31 to acquire image data delivered from the server 2. The image data display controller 32b controls the display unit 33 to display the images based on the image data acquired by the data acquiring unit 32a. The reference information transmission controller 32c controls the data transceiver unit 31 to transmit the reference information generated by the reference information collector 35 to the server 2. The reference information collector 35 generates the reference information on the basis of the process of the image data display controller 32b and the input information of the operation unit 34.

The control unit 42 of the viewer 4 serves as a data acquiring unit 42a, an image data display controller 42b, and a radiographic interpretation information transmission controller 42c. The data acquiring unit 42a controls the data transceiver unit 41 to acquire image data delivered from the server 2. The image data display controller 42b controls the display unit 43 to display the images based on the image data acquired by the data acquiring unit 42a. The radiographic interpretation information transmission controller 42c controls the data transceiver unit 41 to transmit the radiographic interpretation information generated by the radiographic interpretation information collector 45 to the server 2. The radiographic interpretation information collector 45 generates the radiographic interpretation information on the basis of the process of the image data display controller 42b and the input information of the operation unit 44.

The correlation processor 24 of the server 2 is embodied by a computer and the like. The correlation processor 24 serves as an information managing unit 24a and a correlation unit 24b. The information managing unit 24a stores and manages the incidental information, the reference information, and the radiographic interpretation information sent from the image data reception controller 23a and the information reception controller 23c in the information storage 21b. The information managing unit 24a properly sends the managed information to the correlation unit 24b. The correlation unit 24b correlates the present image and the past image on the basis of the information sent from the information managing unit 24a and the correlation information stored in the correlation information database 21c and generates correlation data indicating the correlation result. The correlation unit 24b stores the generated correlation data in the correlation data storage 21d.

Operations of the medical image system 100 having the above-mentioned configuration will be described now.

First, various databases are established in advance in the correlation information database 21c in consideration of the actual configuration or operating type of the medical image system 100 and the information management policy of an operator of the medical image system 100. One of the databases describes the relation between the modality 1 and the viewers 3 and 4. One of the databases describes items of the information used for correlating the images. Another of the databases describes examination frames (examination time zones) of the examination rooms.

FIG. 7 is a diagram illustrating an example of a database describing the relation between the modality 1 and the viewers 3 and 4.

In this embodiment, the modality 1 and the viewers 3 and 4 installed in the same examination room are made to correspond to each other. In the database shown in FIG. 7, information on the modality 1 and the viewers 3 and 4 disposed in the examination rooms is described to correspond to the numbers of the examination rooms. In this embodiment, a device type and an AE (Application Entity) title of the modality 1 are described. As the device type, a type difference such as the X-ray CT device or the MRI device is described. The AE title is an identifier of the devices in the DICOM communication and is given to the modalities 1 to identify one or more modalities 1 belonging to the medical image system 100. Regarding the viewers 3 and 4, the device names and the MAC addresses are described. As the device names, names given to the viewers 3 and 4 so as to identify the plural viewers 3 and 4 belonging to the medical image system 100 are described. As the MAC addresses, addresses given to the viewers 3 and 4 so as to identify the viewers 3 and 4 in the LAN 5 are described.

For example, when the number of examination room 6 shown in the upside of FIG. 1 is 1, it is described in the database shown in FIG. 7 that the modality 1 installed in the examination room 6 is the X-ray CT device and the AE title given to the modality 1 is "TO_CT_CLIN_A." In the database shown in FIG. 7, it is described that names of "viewer 1" and viewer 2" are given to two viewers 3 installed in the examination room 6 and the MAC addresses of "12_34_AB_CD" and "56_78_EF_GH" are given to the viewers.

FIG. 8 is a diagram illustrating an example of the database describing the items of the information used for correlating images.

In this embodiment, the database describes the items of the information used for correlating the images photographed by the modality 1 every device type of the modality 1. For example, in order to correlate the images obtained by the X-ray CT device, it is described to use information on the items such as contrast agent, imaging site, imaging direction, reconstruction function, slice thickness, helical pitch, tube current, and tube voltage. The database describes that the priority order of the items used for correlating the images is as described therein.

FIG. 9 is a diagram illustrating an example of the database describing examination frames for each examination room.

In this embodiment, the database describes the time zones assigned to the examination rooms 6 for doing one examination of the respective examination rooms 6 as the examination frames.

The image data acquired by the photographing of the modality 1 are transmitted to the server 2 under the control of the image data transmission controller 15a as needed. The image data are received and stored in the image database 21a under the control of the image data reception controller 23a. In general, one or more images are obtained in one series. Images corresponding to plural series may be often obtained in one study. Accordingly, the image data are managed as the layers of examination (study), series, and image in the image database 21a. That is, the image data stored in the image database 21a can be individually specified by the examination identification information (examination UID) uniquely indicating the examination, series unique identification information (series UID) unique to the series in the examination, and series numbers indicating the imaging order in the series.

When an examination request is input to one modality 1 from a radioactive information system not shown and connected to a network, a user (a radiology or a radiologist) operates the operation unit 34 while viewing the display of the display unit 33 of the viewer 3 installed in the same examination room as the modality 1, and displays the image (past image) obtained in the past examination of the patient on the viewer 3 on the basis of the patient information (patient ID) of the present examination. The user determines the imaging conditions on the basis of the past image.

In performing such an operation, the reference information collector 35 of the viewer 3 used by the user specifies what time a past image is referred to and generates the reference information indicating it. The reference information includes information such as an image generating condition or the imaging plan determined for the present examination on the basis of the past images, in addition to the past image information (examination UID, series UID, and series number), patient ID, reference date and time, and reference order.

Figure 10:
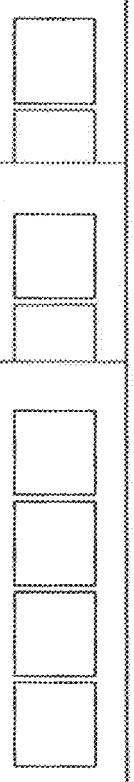
FIG. 10 is a diagram illustrating an example of a display picture in the viewer 3 in FIG. 1 for determining an imaging condition and the like in the present examination while referring to the past images.

FIG. 10 is a diagram illustrating an example of a display screen of the viewer 3 for determining the imaging condition and the like of the present examination while referring to the past images.

The display screen is provided with an input column 72 for inputting the imaging order in the present examination under the condition determined on the basis of the past images to correspond to the referred past images 71. The inputting of the imaging order to the input column 72 is performed by the user operating the operation unit 34. The reference information collector 35 also employs the imaging order input to the input column 72 as the reference order of the past images 71. Accordingly, the reference order is matched with the series imaging order (corresponding to the series number) in the present examination or the series transmission order of the present image from the modality 1 to the server 2. The date and time when the past images are selected as a reference target can be used as the reference date and time. Since one or more past images may be referred to after the past images as the reference target are selected, the time when the past images are selected may be different from the time when the past images are actually referred to. Accordingly, it is preferable that the time when the operation is performed by allowing the user to operate the operation unit 34 to notifying the reference fact is used as the reference time.

The display screen shown in FIG. 10 is provided with a frame to input or select the imaging plan (imaging protocol) or the imaging information (imaging condition, imaging direction, and reconstruction condition) of the present examination, and the information may be collected as a part of the reference information without specifying the imaging order.

When the user is allowed to input the imaging order or the series transmission the modality 1, the reference information collector 35 of the viewer 3 may inquire the modality 1 of the imaging order or the series transmission order of the present examination to acquire the information and may automatically set the information as the initial value of the imaging order in the input column 72. Accordingly, it is possible to simplify the user's work. When the series transmission order is fixed for each modality 1, for example, a database shown in FIG. 11 may be prepared in the correlation information database 21c of the server 2 and the viewer 3 may acquire the information from the server 2.

When the user inputs the imaging plan or the imaging information in the present examination, the viewer 3 can display optional items of the imaging plan or the imaging information regarding the modality used for the imaging and can allow the user to select the imaging plan or the imaging information from the optional items. In this case, for example, as shown in FIGS. 12 and 13, a database describing relations of the imaging plan or the imaging information regarding the modalities 1 between the plural modalities 1 is prepared in the correlation information database 21c and the viewer 3 acquires the information of the database from the server 2. However, since the examination rooms of the present examination and the past examination, the version of the modality, the vendor of the modality, or the imaging information or the imaging plan thereof may vary in the present examination and the past examination. Accordingly, before the imaging plan or the imaging information of the present examination is displayed in the viewer 3, the display information (specifically, character strings displayed in the operation unit) is properly changed. In the change, a database, which is, for example, shown in FIGS. 14 and 15, describing the correspondence of the imaging plan or the imaging condition between the versions or vendors of the same type of modalities is prepared in the correlation information database 21c and the viewer 3 acquires the information of the database from the server 2.

The reference information transmission controller 32c generates the reference information including information collected as described above. The reference information transmission controller 32c includes the information on the imaging order as the reference order in the reference information. The reference information is transmitted to the server 2 under the control of the reference information transmission controller 32c. The server 2 receives the reference information under the control of the information reception controller 23c and the reference information is sent to the information managing unit 24a. At this time, in the data transceiver unit 22 of the server 2, the reference information is reconstructed from the packets including the reference information by inverse encapsulation and the MAC address of the viewer 3 as the transmission source is also extracted. The MAC address is sent to the information managing unit 24a. The information managing unit 24a stores the reference information in the information storage 21b to correspond to the MAC address. FIG. 16 is a diagram illustrating an example of the storage state of the reference information in the information storage 21b.

The imaging of the modality 1 in the present examination is carried out with the imaging plan or the imaging condition determined with reference to the past images. The imaging plan or the imaging condition may be input to the modality 1 by the user or may be input by notifying the imaging plan or the imaging condition input to the viewer 3 from the viewer 3 to the modality 1 through the LAN 5. The reference information may be sent from the viewer 3 or the server 2 to the modality 1 so as to notify the imaging plan or the imaging condition from the viewer 3 to the modality 1.

Figure 17:
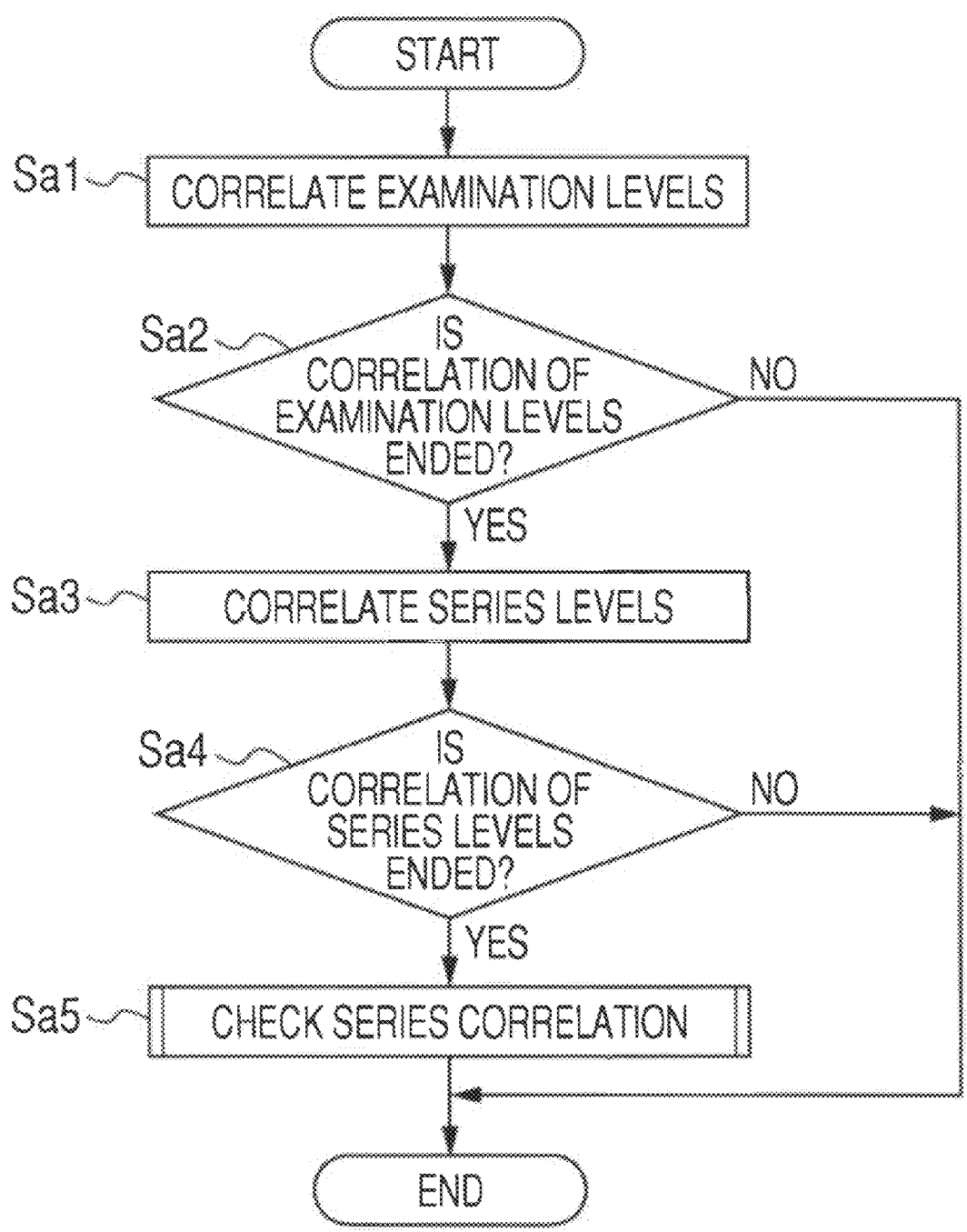
FIG. 17 is a flowchart illustrating a flow of a correlation process in a correlation processor 24.

When the image data of the present image transmitted from the modality 1 is received by the server 2, the correlation processor 24 starts the correlation process in response to the request from the control unit 23. FIG. 17 is a flowchart illustrating a flow of the correlation process in the correlation processor 24.

The correlation process is a process of correlating the received present image with the referred past image.

In step Sa1, the correlation processor 24 performs the correlation process at the examination level. That is, the correlation processor specifies the past examination to be correlated in the present examination. Accordingly, the correlation processor 24 first checks whether the reference information associated with the reference to the past images for the present examination is stored in the information storage 21b. Specifically, the correlation processor 24 first confirms whether the reference information on the past images satisfying the following first and second requirements is stored in the information storage 21*b*.

The first requirement is that the past image relates to the same patient as the present image. This is determined depending on whether the reference information including the same patient ID as the patient ID included in the incidental information of the present image is stored.

The second requirement is that the past image is referred to by the viewer 3 installed in the same examination room 6 as the modality 1 obtaining the present image. This is determined depending on whether the reference information is stored to be correlated with the MAC address which is retrieved from the database shown in FIG. 7 using the AE title of the modality 1 as the transmission source of the present image as a key.

When plural past images satisfying the two requirements exist, it is confirmed whether the reference information of the past image additionally satisfying the following third requirement is stored in the information storage 21*b*.

The third requirement is that the past image is referred to in the examination frame when the present image is obtained. This is determined from the database shown in FIG. 9 and including the imaging date and time of the present image and is also determined depending on the reference information including the reference date and time in the examination frame is stored. However, with the third requirement, it is defined as an operating rule that the past image for the present examination is referred to in the examination frame assigned to the present examination. When such a rule is not applied, it is preferable that the third requirement is not applied. Strictly applying the rule, when the number of past images satisfying the first and second requirements is 1, the third requirement may be applied.

When the corresponding reference information is stored, the correlation processor 24 correlates the past examination associated with the reference information with the present examination. The specific information for the examination correlation is the patient ID and the examination UIDs of the present examination and the past examination.

In step Sa2, the correlation processor 24 confirms whether the correlation at the examination level is completed. When the past examination to be correlated with the present examination cannot be specified, the correlation processor 24 ends the process by setting "no examination correlation information." However, when the correlation at the examination level is finished, the correlation processor 24 guides the process flow from step Sa2 to step Sa3.

In step Sa3, the correlation processor 24 performs the correlation process at the series level. That is, the correlation processor 24 correlates the series included in the present examination and the past examination correlated in step Sa1. Specifically, the correlation processor refers to the image generating condition (WW/WL, slice thickness, and reconstruction function) and the imaging condition (tube current and tube voltage, for example, when the modality 1 is the X-ray CT device) in the incidental information of the past and present series images. The reference is performed in the priority order described in the database shown in FIG. 8. The correlation processor 24 correlates the series having the same image generating condition and the same imaging condition with each other. The plural series having the same image generating condition and the same imaging condition may be included in one examination. Accordingly, in this case, the correlation processor 24 further refers to the imaging order of the plural series in the present examination and the reference order described in the reference information. Then, the correlation processor correlates the series having the same imaging order and the same reference order with each other. In some modalities 1, the series transmission order may be different from the imaging order. Accordingly, the imaging order of the present series is determined with reference to the database shown in FIG. 11. When one or more information is referred to and the series of the present examination to be correlated with the past image is specified, the correlation process may be ended without referring to the other information. The series correlating information includes the series UIDs of the present examination and the past examination.

A specific example of specifying the examination and series to be correlated will be described now. Here, it is assumed that the combination of the image incidental information and the reference information in the present image and the past image is shown in FIG. 18. First, the patient ID is referred to. In this example, since the patient IDs are the same, the examination to be correlated cannot be specified on the basis of the patient ID. Then, the examination room is specified using the database shown in FIG. 7. In this example, since the examination rooms are the same, the examination to be correlated cannot be specified on the basis of the examination room. Then, the examination time zone is referred to using the imaging date and time, the reference date and time, and the database shown in FIG. 9. In FIG. 18, present examination A and past examination C in the same examination frame and present examination B and past examination D in the same examination frame can be specified at the examination levels. In this way, the examinations to be correlated can be specified.

Then, the series to be correlated is specified. In present examination A and past examination C, the image generating condition of the present examination and the image generating condition input at the time of referring to the past image are matched in series 1 to 3. Accordingly, in present examination A and past examination C, series 1 of present examination A and series 1 of past examination C, series 2 of present examination A and series 2 of past examination C, and series 3 of present examination A and series 3 of past examination C are specified, respectively.

On the other hand, in present examination B and past examination D, since the image generating condition is not input at the time of referring to the past examination (in the present examination), the series cannot be specified as described above. Accordingly, the series is specified on the basis of the database shown in FIG. 8. Referring to the image incidental information of the past image, since the information on the contrast (contrast agent) with the first priority is not added to the database shown in FIG. 8 and the information on the imaging site with the second priority is the same as present examination B, the series cannot be specified from the information on the items. Then, it is tried to specify the series using the reconstruction function with the third priority. Since the image generating condition exists in present examination B, the relations of the imaging direction and the reconstruction function are acquired from the device type (modality), the imaging site, and the image generating condition in the database shown in FIG. 12. Referring to the imaging directions of present examination B and past examination D, series 2 of present examination B is matched with series 3 of past examination D. Series 1 and 3 of present examination B and series 1 and 2 of past examination D are matched with each other in imaging direction, but the series cannot be specified therefrom. Then, the reconstruction function is referred to. In this case, series 1 of present examination B and series 2 of past examination D and series 3 of present examination B and series 1 of past examination D are specified as the series to be correlated.

In step Sa4, the correlation processor 24 confirms whether the correlation process at the series level is finished. When the series to be correlated cannot be specified in the present examination and the past examination, the correlation processor 24 ends the process by setting "no series correlating information." However, when the correlation at the series level is finished, the correlation processor 24 guides the process flow from step Sa4 to step Sa5.

In step Sa5, the correlation processor 24 performs a checking process of checking the validity of the correlation performed hitherto.

Figure 19:
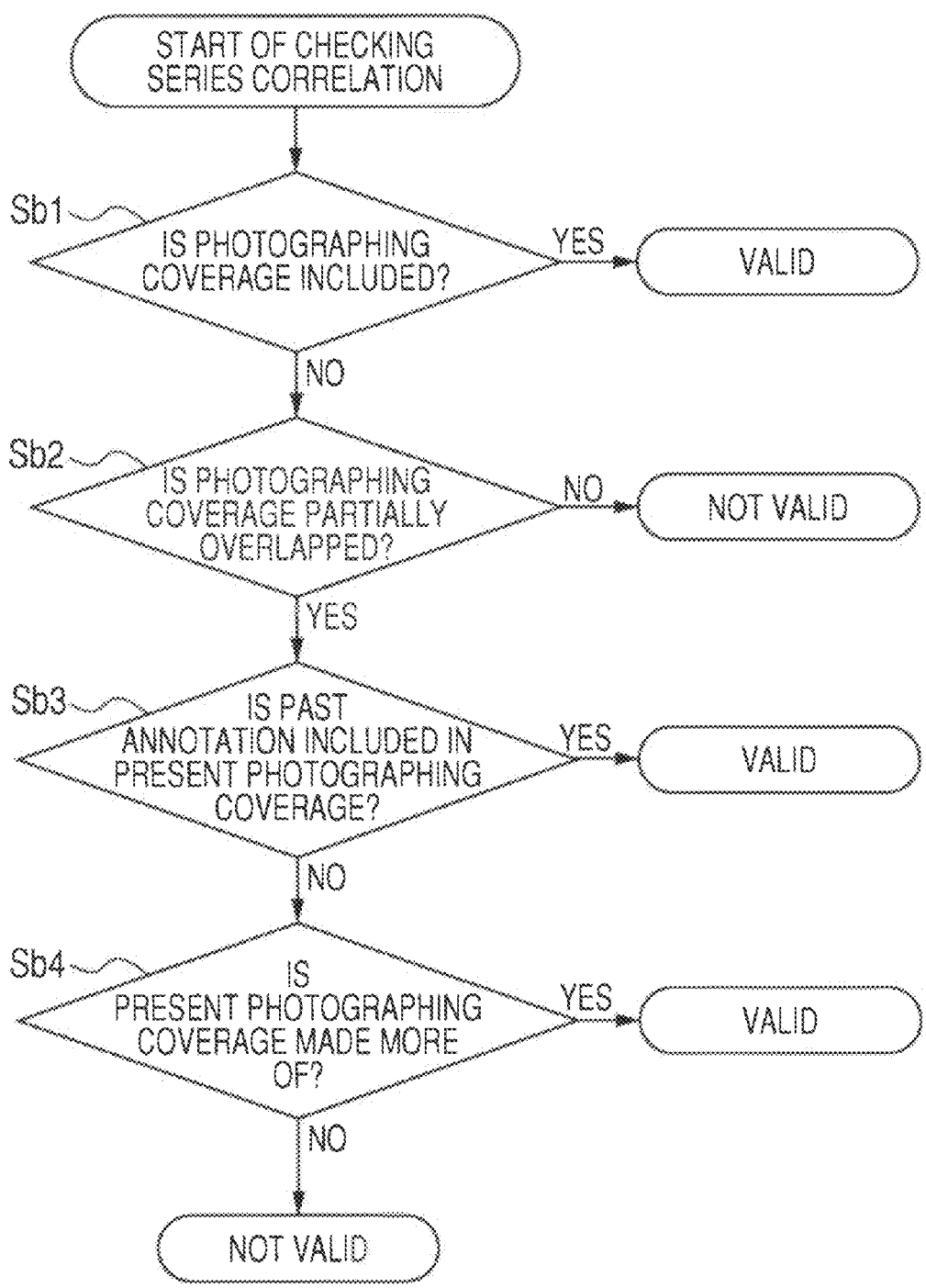
FIG. 19 is a flowchart illustrating a flow of a check process in the correlation processor 24.

FIG. 19 is a flowchart illustrating a flow of the check process in the correlation processor 24.

In step Sb1, the correlation processor 24 confirms whether one of the coverage of the present image and the coverage of the past image is included in the other in the series combination of the present image and the past image. For example, when the modality 1 is the X-ray CT device, the coverage recorded in a scanogram can be used for the confirmation. However, when the scanogram is not included in the examination image, the series images can be analyzed by CAD (Computer Aided Detection) to reconstruct a scanographic image and to acquire the coverage or the volume can be reconstructed to generate a coronal image (corresponding to the scanographic image). When the scanographic image is included, the correlation processor 24 determines that the correlation is valid and then ends the check process.

Otherwise, the correlation processor 24 guides the process flow from step Sb1 to step Sb2.

In step Sb2, the correlation processor 24 confirms whether the coverage of the present image and the coverage of the past image are partially matched with each other in the series combination of the present image and the past image. When the coverages are not matched, the correlation processor 24 determines that the correlation is not valid and ends the check process. However, when the coverages are partially matched, the correlation processor 24 guides the process flow from step Sb2 to step Sb3.

In step Sb3, the correlation processor 24 confirms whether the position of the past image to which annotation is added is included in the coverage of the present image. The addition of the annotation to the past image can be necessarily known from the image incidental information. When the position of the past image to which the annotation is added is included in the coverage of the present image, the correlation processor 24 determines that the correlation is valid and ends the check process. Otherwise, the correlation processor 24 guides the process flow from step Sb3 to step Sb4.

In step Sb4, the correlation processor 24 confirms whether the coverage of the present image is set to make much of. Before starting the examination, the user sets which of the coverage of the present examination series and the coverage of the past examination series to make much of. When the coverage of the present examination series is set to make more of than the coverage of the past examination series, the correlation processor 24 determines that the correlation is valid and ends the check process. Otherwise, the correlation processor 24 determines that the correlation is not valid and ends the check process.

A specific example of the check process will be described now.

Figure 20:
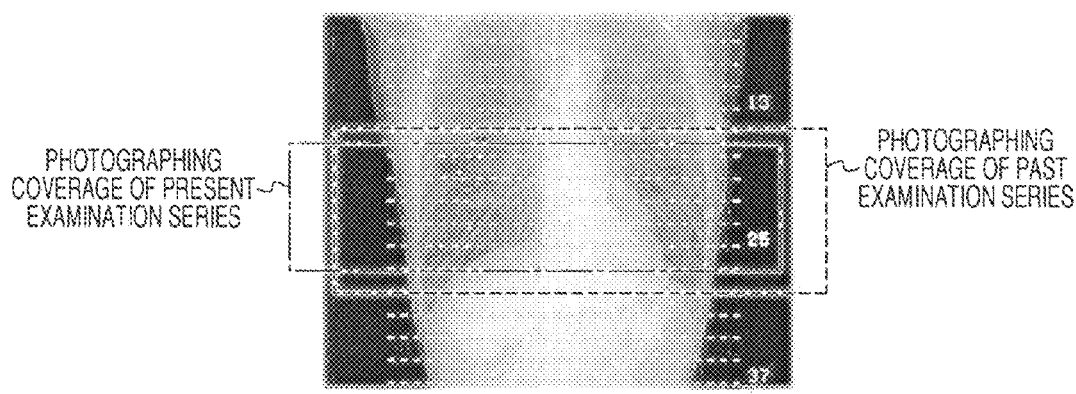
FIG. 20 is a diagram illustrating an example of a relation in imaging coverage between a past examination series and a present examination series.

In the example shown in FIG. 20, since the coverage of the past examination series includes the coverage of the present examination series, it is determined by the determination of step Sb1 that the correlation is valid. On the contrary, even when the coverage of the present examination series includes the coverage of the past examination series, it is determined that the correlation is valid.

Figure 21:
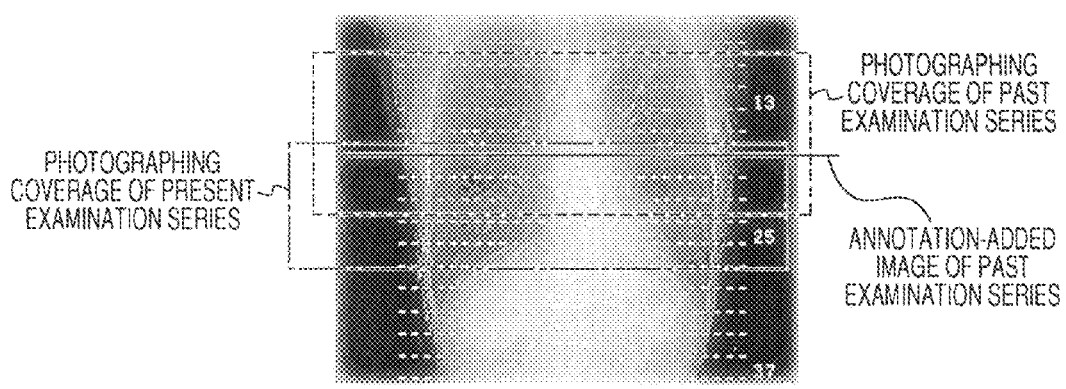
FIG. 21 is a diagram illustrating an example of a relation in imaging coverage between a past examination series and a present examination series.

In the example shown in FIG. 21, the coverage of the past examination series and the coverage of the present examination series do not have any inclusion relation (the relation that the coverages are not included in each other), but the coverages are partially matched. In the example shown in FIG. 21, since the position of the annotation image of the past examination series is included in the coverage of the present examination series, it is determined by the determination of step Sb3 that the correlation is valid.

When the coverage of the present examination series does not include the position of the annotation image of the past examination series below the position shown in FIG. 21 and the coverage of the present examination series is set to make more of than the coverage of the past examination series, it is determined that the correlation is valid. Otherwise, it is determined that the correlation is not valid.

When it is determined in the check process that the correlation is not valid, the correlation processor 24 retries the correlation at the series level in step Sa3, or discards the process result and does not perform the correlation process of the present examination series and the past examination series.

When it is determined that the correlation is valid, the correlation processor 24 stores the correlation information such as patient ID and examination UIDs and series UIDs of the present examination and the past examination in the database shown in FIG. 22. The database shown in FIG. 22 is established in the correlation data storage 21*d*. The information on the present image and the past image not correlated is stored in the correlation data storage 21*d*.

When plural examinations are made on a patient, the same process is repeated on the images obtained in the examinations and the images are correlated with the past images, respectively. For example, when three examinations are made and are denoted in time series by examination A1, examination A2, and examination A3, examination A1 is correlated with examination A2, examination A2 is correlated with examination A3, and thus examination A3 and examination A1 are indirectly correlated with each other.

When requests for displaying the images of the present examination are given from the viewers 3 and 4, the image data delivery unit 23*b* delivers the image data of the present image, the correlation information on the present image, and the image data of the past image included in the correlation information to the viewers 3 and 4. The viewers 3 and 4 display the present image and the past image correlated with each other in parallel on the screen on the basis of the image data and the correlation information delivered as described above. In the correlation process, when all or a part of the correlation information on the present image is omitted, the present image and the past image are displayed (in a thumbnail display manner) in the unit of series.

When the comparison image at the time of interpreting the present image is changed to the past image not included in the correlation information by the radiologist, the radiographic information collector 45 of the viewer 4 collects the examination and series information of the past image and generates change information including the collected information. The change information is transmitted to the server 2 under the control of the radiographic interpretation information transmission controller 42*c*. The server 2 receives the change information under the control of the information reception controller 23*c* and sends the received change information to the correlation processor 24. The correlation processor 24 updates the correlation data stored in the correlation data storage 21*d* on the basis of the change information.

According to this embodiment, the correlation between the image obtained by the modality 1 and the image referred to by the viewer 3 for obtaining the image is automatically performed by the server 2 and the correlation information indicating the correlation result is stored in the memory unit 21 of the server 2. When an image correlated with another image is requested on the basis of the correlation information, the server 2 can allow the viewer 4 and the like to compare and confirm the correlated images by delivering the requested image along with the image correlated thereto. Accordingly, in the diagnosis for observing the progress, since the radiologist need not extract the past images suitable for comparison with the image of the present examination, it is possible to improve the radiographic interpretation efficiency.

According to this embodiment, when one of the images compared and displayed is changed on the basis of the correlation information at the time of interpreting the radiographic image, the correlation information is updated into the details in which the changed images are correlated and thus the correlation information reflecting the radiographic interpretation result can be properly managed. Accordingly, the images having the more correlation can be referred to in the often image reference.

For example, when the diagnosis is difficult using the past image acquired in the past examination using the CT device, the MRI device may be used for the precise examination in the next examination (present examination). In this case, the present image is obtained with a modality 1 of a type different from that used to obtain the past image referred to by the viewer 3 and the present image and the past image should be correlated with each other. However, according to this embodiment, since the correlation of the examinations is performed depending on the correspondence between the modality 1 and the viewer 3 shown in FIG. 7, it is possible to correlate the past image and the present image, which are acquired by the different types of modalities 1, with each other. However, in this case, the image generating conditions and the imaging conditions are different in the past image and the present image. Therefore, the reference of the image generating conditions and the imaging conditions is omitted and the series is correlated with reference to the reference information and the projection order of the series of the present image.

This embodiment can be modified in various forms as described below.

(1) The modality 1 may acquire the information indicating the imaging order and the imaging plan (imaging protocol) input to the viewer 3 or the imaging information (imaging condition, imaging direction, and reconstruction condition) from the viewer 3 and may perform the imaging operation or the image generating operation (image reconstructing operation) on the basis of the acquired information. For example, the series numbers of the series images in the present examination are added in the imaging order set in the viewer 3. It is preferable that the reconstruction conditions are used at the time of generating an image so as to correspond to the imaging order, that is, the series numbers, set in the viewer 3.

(2) In the above-mentioned embodiment, the AE title and the MAC address are used to specify the relation among the examination room 6, the modality 1, and the viewer 3. However, as long as the physical position relation among the examination room 6, the modality 1, and the viewer 3 can be specified, an IP address may be used instead of the AE title and the MAC address. In this case, the IP address is preferably a fixed IP address. However, a dynamic ID address managed by a DHCP (Dynamic Host Configuration Protocol) server can be used to specify the device relation. When host names (host IDs) are assigned to the modality 1, the server 2, and the viewer 3, the host names (host IDs) can be used.

(4) The time for starting the correlation process may be optional. For example, the time with a constant time interval such as fixed times, predetermined times in the night, or the time when the processing load of the server 2 is reduced can be set as the start time.

(5) In the correlation at the series level, the reference order determined depending on the reference date and time may be combined with the series transmission order. In this case, the user need not specify the imaging order in the viewer 3. When one of the reference date and time and the reference order cannot be collected due to a certain reason, the order determined from the collected information can be combined with the series transmission order. The reference date and time and the reference order may not be matched with the actual order for referring to the images depending on the detection methods thereof. Accordingly, the reference order to be combined with the series transmission order is preferably determined depending on the information accurately indicating the actual order for referring to the image.

(6) Although the server 2 has the function of storing and managing the image data and the correlation function, particular devices individually having the functions may be provided.

(7) Many types of modalities 1 obtain plural series in the order in which the image generating conditions and the imaging conditions for the series are set. When the image generating conditions and the imaging conditions based on the reference are set in the reference order of the past images, the imaging order and the reference order are always matched with each other. Accordingly, when all the modalities 1 included in the medical image system 100 are of such a type and it is established as an operation rule of the medical image system 100 that the image generating conditions and the imaging conditions are set in the reference order of the past images, the correlation process at the series level can be performed only with reference to the imaging order and the reference order.

(8) The modality 1 may notify the viewers 3 and 4 of the information indicating the imaging condition of at least one series in the present examination. In this case, the viewers 3 and 4 can refer the user to the imaging condition of the at least one series in the present examination on the basis of the information notified from the modality 1.

(9) It is assumed that series 1 to 3 of the past examination for patient A are referred to in the previous examination frame among two continuous examination frames and series 1 to 3 of the past examination for patient B are referred to in the subsequent examination frame. It is assumed that the present examination for patient A is made in the previous examination frame to acquire the images of series 1 to 3 and the present examination for patient B is made in the subsequent examination frame to acquire the images of series 1 to 3. Then, since the user makes the present examination for patient B without re-inputting the patient ID in the modality 1, the images acquired in the present examination for patient B may be included as the images of series 4 to 6 in the present examination for patient A. In this case, conventionally, the user edits the series to cut out the series and re-registers the cut-out series in the image management device in a different examination.

However, in this embodiment, since the patients of the past examination and the present examination are not matched with each other in the subsequent examination frame, the examinations cannot be correlated with each other. Therefore, the series can be divided on the basis of the correlation result to urge the user to perform the edition on the present image of the different examination, or can be automatically divided. In this case, it can be estimated by reference to the examination frame that series 4 to 6 correspond to series 1 to 3 of the present examination for patient B. The estimation result may be provided to the user or the division and correlation may be automatically carried out on the basis of the estimation result.

(10) It is assumed that series 1 to 4 of the past examination for patient A are referred to in the previous examination frame of two continuous examination frames and series 1 to 3 of the past examination for patient B are referred to in the subsequent examination frame. It is assumed that the present examination for patient A is made from the previous examination frame up to the examination gap between the previous examination frame and the subsequent examination frame to acquire the images of series 1 to 4 and the present examination for patient B is made in the subsequent examination frame to acquire the images of series 1 to 3. Here, since the user makes the present examination for patient B without re-inputting the patient ID in the modality 1, it is assumed that the images acquired in the present examination for patient B are included as the images of series 5 to 7 in the present examination for patient A. However, it is assumed that the image of series 4 is acquired in the examination gap between the previous examination frame and the subsequent examination frame.

In this case, the images of series 4 to 7 cannot be correlated at the examination level on the basis of the patient ID and the examination frame. Accordingly, the longest examination time is defined in advance as the time longer than the time of one examination frame. When there is a series not to be correlated, the series obtained in the longest examination time are considered as being obtained in the previous examination frame and thus correlated. Then, it is possible to correlate the images obtained out of the original examination frame. For example, when the longest examination time is defined as the time of the examination frame+the examination gap in the above-mentioned case, series 4 is treated as one of the series of the present examination made in the previous examination frame and can be correlated with the series of the past examinations. Series 5 to 7 can be properly processed by the use of the technique of (9).

(11) It is assumed that the reference information of series 1 to 4 in the past examination is stored in the server 2 and that only series 1 and 2 in the present examination are normally transmitted and series 3 and 4 in the present examination are not transmitted due to a certain communication failure when the series (information such as patient ID and imaging time is all included) in the present examination are transmitted from the modality 1 to the server 2.

In this case, the correlation processor 24 starts the correlation process, but it is not preferable that the correlation processor performs the correlation process in this state, because there is an image of the present examination having the reference information and the patient ID included in the reference information. Accordingly, the shortest examination time is defined and it is assumed that the present examination ended in the examination time shorter than the minimum examination time is not subjected to the correlation process. For example, when the minimum examination time is 20 minutes and the examination time for imaging series 1 and 2 is 10 minutes, the examination time of the present examination is shorter than the minimum examination time. Accordingly, the correlation processor 24 does not perform the correlation process on the present examination. When it is determined that the examination time is greater than 20 minutes due to the transmission of the images of series 3 and 4 from the modality 1, the correlation processor 24 can start the correlation process on the present examination.

(12) It is assumed that series 1 and 2 in the past examinations for patient A and patient B are referred to in the same examination frame. It is also assumed that the user does not input the patient ID or images patient B with the patient ID of patient A set to acquire the images of series 1 to 4.

In this case, when the minimum examination time is defined as the time required for obtaining the images of two series, series 1 to 4 in the present examination includes the series corresponding to two examinations. Accordingly, since it can be estimated that an examination boundary exists between series 2 and series 3, the series may be divided to urge the user to perform the editing process on the present image of a different examination or may be automatically divided.

(13) In the second requirement in the above-mentioned embodiment, the modality 1 and the viewer 3 installed in the same examination room 6 are made to correspond to each other. However, the second requirement may be determined so that the modality 1 and the viewer 3 having a different relation are made to correspond to each other. For example, plural examinations may be planned by the use of one viewer 3 in the morning. In this case, the viewer 3 is associated with the plural modalities 1 and the past images referred to by the viewer 3 can be correlated with the present images obtained by the plural modalities 1. Therefore, the second requirement is determined so that the plural modalities 1 used for the plural examinations correspond to the viewer 3.

(14) The correlation result is not managed by the database shown in FIG. 22, but an object (referred to as simulated shared object) acquired by simulating shared object (referred to as real shared object) disclosed in Japanese Unexamined Patent Publication 2007-167634 may be prepared and stored.

Figure 23:
FIG. 23 is a diagram illustrating an example of a simulated object.

FIG. 23 is a diagram illustrating an example of the simulated object.

The simulated shared object is generated for each series of the present examination. The simulated shared object includes image information, object-specific information, photographing condition, image generating condition, and key image information.

The image information indicates one or more positioning images (for example, the scanogram in the CT or the coronal image due to the pilot scanning in the MRI) acquired in the present examination including the series. The key image line indicates at what position in the scanned image the image specifying the image serving as a key to the radiographic interpretation is located, when the radiographic images of the present examination are interpreted by the radiologist.

The object-specific information includes object UID, parent object UID, parent series UID, correlated series UID, series information, and object flag.

The object UID indicates the unique number of the corresponding series.

The parent object UID indicates the object UID of the object for the series correlated with the corresponding series. When the shared object does not exist for the series of the past examination, the parent object UID is blank.

The parent series UID indicates the series UID of the series correlated with the corresponding series.

The correlated series UID indicates the series UID of the target series when plural series to be correlated with the series of the present examination exist. When there is no target series, the correlated series UID is blank.

The series information indicates date, time, and series UID of the corresponding series.

The object flag indicates whether the shared object is the real shared object or the simulated shared object. Here, "0" is assigned to the real shared object and "1" is assigned to the simulated shared object.

The imaging condition indicates the imaging condition of the corresponding series.

The image generating condition indicates the image generating condition of the corresponding series.

The key image information indicates information of an image specified as the key image at the time of interpreting the radiographic image of the corresponding series or preparing a report on the image of the corresponding series. In the above-mentioned embodiment, since the correlation process is performed at the examination level and the series level between the past examination and the present examination, the key image is not specified in this step. Accordingly, the key image is blank. By allowing the radiologist to interpret the radiographic image of the examination series and allowing the radiographic interpretation information collector 45 to collect information on whether the key image and the specified image exist, it is possible to update the key image information of the simulated shared object by the use of the correlation processor 24. In a report preparing device using the real shared object, the key image information can be set on the read simulated shared object.

By preparing the simulated shared object described above, the correlation result in the above-mentioned embodiment can be used in devices suitable for the technique disclosed in Japanese Unexamined Patent Publication No. 2007-167634.

However, the real shared object prepared by the use of the technique disclosed in Japanese Unexamined Patent Publication No. 2007-167634 correctly indicates the correlation of examinations or series, but the correlation of examinations or series indicated by the simulated shared object is merely estimated. However, since the real shared object and the simulated shared object are distinguished by the use of the object flag, the shared object can be utilized by considering which of the real shared object and the simulated shared object the shared object is.

By setting the numbering system (numbering rule) of the object UID to be different between the real shared object and the simulated shared object, the real shared object and the simulated shared object may be made to be distinguishable on the basis of the object UID. In this case, the object flag can be deleted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image managing device used in a medical image system in which an image storage device storing medical images obtained by an imaging device as past images so as to specify an examination and a series of images and one or more image reference devices referring a user to the past images stored in the image storage device are connected to each other through a network, the medical image managing device comprising:

an examination correlating unit configured to correlate one past examination with a present examination, the correlated past examination being an examination on the past images satisfying two requirements that (1) the past examination is referred to by the image reference device correlated in advance with the imaging device among the one or more image reference devices and that (2) a patient to be imaged is the same; and a series correlating unit configured to correlate a series of images included in the present examination and the past examination correlated by the examination correlating unit with each other with reference to imaging conditions of the respective series.

2. The medical image managing device according to claim 1, wherein the examination correlating unit correlates the examination for the past image, which is referred to by the image reference device in the same time zone in which the present examination is made, with the present examination when one or more examinations for the past image satisfying the two requirements exist.

3. The medical image managing device according to claim 1, wherein the examination correlating unit does not correlate the present examination and the past examination made in different time zones with each other.

4. The medical image managing device according to claim 1, wherein the examination correlating unit treats the series, which is acquired out of the time zone assigned to make one examination and within the longest imaging time, as being acquired in the present examination made in the previous examination time zone.

5. The medical image managing device according to claim 1, wherein the examination correlating unit does not perform the correlation process on the present examination which is ended in an examination time shorter than the shortest examination time.

6. The medical image managing device according to claim 1, wherein the series correlating unit correlates the series with reference to at least one of an image generating condition and an imaging condition.

7. The medical image managing device according to claim 6, wherein when a plurality of sets of series of which the at least one of the image generating condition and the imaging condition is matched exists, the series correlating unit correlates the series with reference to an imaging order of each series in the imaging device and a reference order of each series in the image reference device.

8. The medical image managing device according to claim 1, wherein the series correlating unit correlates the series with reference to an imaging order of each series in the imaging device and a reference order of each series in the image reference device.

9. The medical image managing device according to claim 1, wherein the series correlating unit refers to a plurality of imaging conditions in a predetermined order.

10. The medical image managing device according to claim 1, further comprising a unit configured to generate correlation information indicating the correlation results of the examination correlating unit and the series correlating unit.

11. The medical image managing device according to claim 1, further comprising a request unit configured to request the image storage device to deliver the past image of the series correlated with the series of the medical image to be delivered on a basis of the correlation information on the examination along with the medical image to be delivered in response to the delivery request of the medical image of the series in the examination, after the medical image in the present examination is stored as the past image in the image storage device.

12. The medical image managing device according to claim 11, further comprising, in response to the request to the image storage device for change and delivery of an image of one of the series delivered by the image storage device in response to the request from the request unit, a unit configured to update the correlation information so as to correlate the series of the image to be changed and delivered with the other of the series delivered by the image storage device in response to the request from the request unit.

13. The medical image managing device according to claim 1, further comprising a check unit configured to determine that the correlation of the series correlating unit is valid when coverage of one of the series correlated by the series correlating unit is included in coverage of the other series.

14. The medical image managing device according to claim 1, further comprising a check unit configured to determine that the correlation of the series correlating unit is valid when coverage of one of the series correlated by the series correlating unit is partially matched with coverage of the other series and an imaging position of the past image having annotation added thereto is included in the coverage of the series in the present examination.

15. The medical image managing device according to claim 1, further comprising a check unit configured to determine that the series in the present examination is not appropriate when only some series of the present examination is not correlated with the series of the past examination by the series correlating unit.

16. The medical image managing device according to claim 1, further comprising a check unit configured to determine that the plurality of series is acquired from a plurality of examinations when the time required for imaging the plurality of series acquired in the present examination is greater than the shortest examination time.

17. The medical image managing device according to claim 13, further comprising a unit configured to send the determination result of the check unit to a user.

18. The medical image managing device according to claim 1, further comprising a preparation unit configured to prepare an information object indicating the correlation result of the series correlating unit.

19. The medical image managing device according to claim 18, wherein the preparation unit includes information for identifying that the correlation result is based on presumption in the information object.

20. A medical image system comprising:
one or more imaging devices obtaining medical images;
an image storage device storing the medical images obtained by the imaging devices as past images so as to specify an examination and a series;
one or more image reference devices referring a user to the past images stored in the image storage device; and
a medical image managing device,
wherein each imaging device includes an incidental information generating unit configured to generate incidental information, which includes imaging device identification information for identifying the corresponding photographing imaging device, patient identification information for identifying a patient, and condition information indicating imaging conditions of the series, for each examination,
wherein each image reference device includes a reference information generating unit configured to generate reference information, which includes reference device identification information for identifying the image reference device and image identification information for identifying past images referred to by the user, for each examination,
wherein the medical image managing device includes
an acquisition unit configured to acquire the incidental information and the reference information,
an examination correlating unit configured to correlate the examinations corresponding to the incidental information and the reference information with each other, when two requirements that (1) the imaging device and the image reference device specified on the basis of the incidental information and the reference information acquired by the acquisition unit are correlated in advance and that (2) a patient specified on the basis of the incidental information acquired by the acquisition unit is equal to a patient specified on the basis of the reference information acquired by the acquisition unit, and
a series correlating unit configured to correlate a series with reference to the photographing imaging condition specified on the basis of the incidental information acquired by the acquisition unit and the imaging condition specified by the reference information acquired by the acquisition unit.

21. The medical image system according to claim 20, further comprising a setting unit disposed in the image reference device and configured to set an imaging condition of the present examination of the imaging device in response to the user's instruction when the user is referred to the past images.

22. The medical image system according to claim 21, further comprising a unit configured to notify the imaging device of the condition set by the setting unit.

23. The medical image system according to claim 21, further comprising a storage unit configured to store at least one imaging condition of the imaging device,
wherein the setting unit sets the imaging conditions specified by the user as the imaging condition associated with the present examination among the conditions stored in the storage unit.

24. The medical image system according to claim 23, further comprising a unit disposed in the imaging device and configured to notify the image reference device of information indicating the imaging condition of at least one series in the present examination.

25. The medical image system according to claim 23, further comprising a unit disposed in the image reference device and configured to refer the user to the imaging condition of at least one series in the present examination on the basis of the information notified obtained from the imaging device.

* * * * *